United States Patent
Xiao

(10) Patent No.: US 8,318,252 B2
(45) Date of Patent: Nov. 27, 2012

(54) ANTIMONY PRECURSORS FOR GST FILMS IN ALD/CVD PROCESSES

(75) Inventor: Manchao Xiao, San Diego, CA (US)

(73) Assignee: Air Products and Chemicals, Inc., Allentown, PA (US)

(*) Notice: Subject to any disclaimer, the term of this patent is extended or adjusted under 35 U.S.C. 154(b) by 608 days.

(21) Appl. No.: 12/355,325

(22) Filed: Jan. 16, 2009

(65) Prior Publication Data

US 2009/0191330 A1 Jul. 30, 2009

Related U.S. Application Data

(60) Provisional application No. 61/023,989, filed on Jan. 28, 2008.

(51) Int. Cl.
*C23C 16/06* (2006.01)
*C07F 7/08* (2006.01)
*C07F 7/30* (2006.01)
*C07F 9/90* (2006.01)

(52) U.S. Cl. ............. 427/255.29; 427/250; 427/255.28; 427/255.395; 556/64; 556/81

(58) Field of Classification Search .................. 427/124, 427/250, 255.28, 248.1, 255.29, 255.395; 556/9, 12, 64, 81
See application file for complete search history.

(56) References Cited

U.S. PATENT DOCUMENTS

| | | | |
|---|---|---|---|
| 7,105,870 B2 | 9/2006 | Lee et al. | |
| 7,371,429 B2 | 5/2008 | Lee et al. | |
| 7,518,007 B2* | 4/2009 | Seo et al. | 556/12 |
| 7,727,884 B2* | 6/2010 | Bae et al. | 438/631 |
| 7,960,205 B2* | 6/2011 | Xiao et al. | 438/95 |
| 2006/0039192 A1 | 2/2006 | Ha et al. | |
| 2006/0049447 A1 | 3/2006 | Lee et al. | |
| 2006/0072370 A1 | 4/2006 | Kuh et al. | |
| 2006/0094860 A1 | 5/2006 | Take | |
| 2006/0141710 A1 | 6/2006 | Yoon et al. | |
| 2006/0172083 A1 | 8/2006 | Lee et al. | |
| 2006/0180811 A1* | 8/2006 | Lee et al. | 257/40 |
| 2008/0085610 A1* | 4/2008 | Wang et al. | 438/785 |
| 2009/0074652 A1* | 3/2009 | Dussarrat | 423/508 |
| 2009/0112009 A1* | 4/2009 | Chen et al. | 556/12 |
| 2009/0124039 A1* | 5/2009 | Roeder et al. | 438/99 |
| 2009/0305458 A1* | 12/2009 | Hunks et al. | 438/102 |
| 2010/0009078 A1 | 1/2010 | Pore et al. | |

FOREIGN PATENT DOCUMENTS

| | | |
|---|---|---|
| JP | 2006-124262 | 5/2006 |
| JP | 2006-182781 | 7/2006 |
| JP | 2006-182781 A1 | 7/2006 |
| JP | 2006-225390 | 8/2006 |
| WO | 02/065508 A | 8/2002 |
| WO | 2007/133837 A | 11/2007 |
| WO | 2007/133837 A2 | 11/2007 |
| WO | 2008/057616 A | 5/2008 |

OTHER PUBLICATIONS

Lee, et al; "GeSbTe Deposition for the PRAM Application"; Applied Surface Science, Elsevier, Amsterdam, NL; vol. 253, No. 8; Feb. 1, 2007; pp. 3969-3976; XP005868235.
M.R. Detty, et al, Bis(trialkylsilyl) chalcogenides. 1. Preparation and Reduction of Group 6A Oxides, J. Org. Chem. 1982, 47, pp. 1354-1356.
G. Becker et al, Tris(trimethylsily)arsane, -stibane, -bismuthane, (1,2-Dimethyoxyethane-O,O')-lithium . . . , Synthetic Methods of Organometallic and Inorganic Chemistry, 1996, vol. 3, H.H. Karsch, NY, p. 193.
D.H. Busch et al, Inorganic Synthesis, 1980 vol. 20, pp. 171-176.
M.N. Bochkarev et al, Zhurnal Obshchei Khimii 1969, 39, pp. 135-141.
H. Buerger et al, Inorganic and Nuclear Chemistry Letters 1967, 3, pp. 549-552.
Byung Joon Choi et al, Cyclic PECVD of Ge2Sb2Te5 Films Using Metallorganic Sources, J. Elec. Soc. 154 (4) 2007 pp. H318-H324.
Sang-Wook Kim et al, in AsxSb1-x alloy nanocrystals for use in the near infrared, Chem. Commun., 2006, pp. 4811-4813.
Stephan Schulz et al, Synthesis and Characterization of Organogallium-antimony Compounds, J. Organ. Chem. 570, 1998, pp. 275-278.
Byung Joon Choi et al, Combined atomic layer and chemical vapor deposition, and selective growth of . . . , Chem. Mater. 2007, 19, pp. 4387-4389.
Ran-Young Kim et al, Structural properties of Ge2Sb2Te5 thin films by metal organic chemical vapor . . . , App. Phys. Letters 89, 2006, pp. 102107-1 to 102107-3.
Junghyun Lee et al, GeSbTe deposition for the PRAM application, App. Surface Sci. 253, 2007, pp. 3969-3976.
Alexander Sladek et al, Synthesis and crystal and molecular structure of tris(dimethylphenylsilyl) antimony, Chem. Ber. 1995, 128, pp. 565-567.

* cited by examiner

*Primary Examiner* — Matthew Daniels
*Assistant Examiner* — Dennis Cordray
(74) *Attorney, Agent, or Firm* — Joseph D. Rossi; Rosaleen P. Morris-Oskanian

(57) ABSTRACT

The present invention is a process of making a germanium-antimony-tellurium alloy film using a process selected from the group consisting of atomic layer deposition and chemical vapor deposition, wherein a silylantimony precursor is used as a source of antimony for the alloy film. Novel silylantimony compounds are also disclosed.

12 Claims, No Drawings

ANTIMONY PRECURSORS FOR GST FILMS IN ALD/CVD PROCESSES

CROSS REFERENCE TO RELATED APPLICATIONS

The present patent application claims the benefit of US Provisional Patent Application Ser. No. 61/023,989 filed 28 Jan. 2008.

BACKGROUND OF THE INVENTION

As an emerging technology, phase change materials attract more and more interest for their applications in manufacturing a new type of highly integrated, nonvolatile, memory devices: phase change random access memory (PRAM). Phase change random access memory (PRAM) devices are synthesized using materials that undergo a reversible phase change between crystalline and amorphous phases, that have distinctly different resistances. The most commonly used phase change materials are ternary compositions of chalcogenide of group 14 and group 15 elements, such as germanium-antimony-tellurium compounds, commonly abbreviated as GST.

One of the technical hurdles in designing a PRAM cell is that in order to overcome the heat dissipation during the switching of GST materials from crystalline to amorphous states at certain temperatures, a high level of reset current has to be applied. This heat dissipation can be greatly reduced by confining the GST material into contact plugs, that would reduce the reset current needed for the action. To build GST plugs on the substrate, atomic layer deposition (ALD) processes are used to produce films with high conformality and chemical composition uniformity.

Relevant prior art includes:

sang-Wook Kim, S. Sujith, Bun Yeoul Lee, Chem. Commun., 2006, pp 4811-4813.

Stephan Schulz, Martin Nieger, J. Organometallic Chem., 570, 1998, pp 275-278.

Byung Joon Choi, et al. Chem Mater. 2007, 19, pp 4387-4389; Byung Joon Choi, et al. J. Etectrochem. Soc., 154, pp H318-H324 (2007);

Ranyoung Kim, Hogi Kim, Soongil Yoon, Applied Phys. Letters, 89, pp 102-107 (2006).

Junghyun Lee, Sangjoon Choi, Changsoo Lee, Yoonho Kang, Daeil Kim, Applied Surface Science, 253 (2007) pp 3969-3976.

G. Becker, H. Freudenblum, O. Mundt, M. reti, M. Sachs, Synthetic Methods of Organometallic and Inorganic Chemistry, vol. 3, H. H. Karsch, New York, 1996, p.193.

Sladek, A., Schmidbaur, H., Chem. Ber. 1995, 128, pp 565-567.

U.S. patent applications:
US 2006/0049447 A1
US 2006/0039192 A1;
US 2006/0072370 A1; and
US 2006/0172083 A1.

BRIEF SUMMARY OF THE INVENTION

The present invention is a process of making a germanium-antimony-tellurium alloy film using a process selected from the group consisting of atomic layer deposition and chemical vapor deposition, wherein a silylantimony precursor is used as a source of antimony for the alloy film.

Preferably, the present invention is a process of making a germanium-antimony-tellurium alloy film using a process selected from the group consisting of atomic layer deposition and chemical vapor deposition, wherein a silylantimony precursor is used as a source of antimony for the alloy film, wherein the silylantimony precursor is selected from the group consisting of:

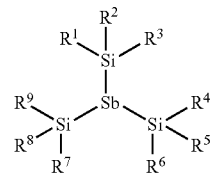
(A)

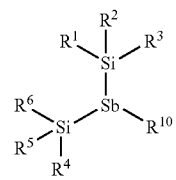
(B)

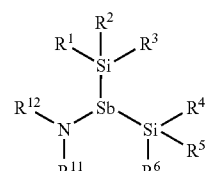
(C)

where $R^{2-10}$ are individually a hydrogen atom, an alkyl group or alkenyl group with 1 to 10 carbons as chain, branched, or cyclic, or an aromatic group; $R^1$ is individually a hydrogen atom, an alkyl group or alkenyl group with 2 to 10 carbons as chain, branched, or cyclic, or an aromatic group; $R^{11}$ and $R^{12}$ are individually an alkyl group or alkenyl group with 1 to 10 carbons as chain, branched, or cyclic, or an aromatic group; and wherein a germanium precursor is an aminogermane with the general formula:

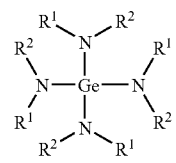

where $R^1$ and $R^2$ are individually alkyl groups with 1 to 10 carbons in chain, branched, or cyclic; and wherein a tellurium precursor is an silylantimony selected from the group consisting of:

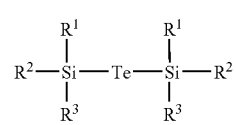
(a)

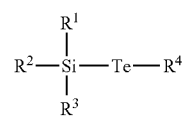
(b)

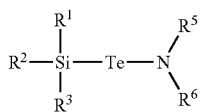
(c)

where $R^1, R^2, R^3, R^4, R^5$, and $R^6$ are independently hydrogen, alkyl groups having 1 to 10 carbons in linear, branched, or cyclic forms with or without double bonds, or aromatic groups.

The present invention is also a composition of matter having the general structure selected from the group consisting of:

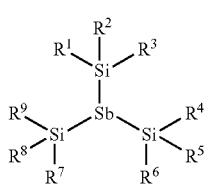
(A)

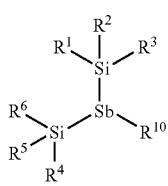
(B)

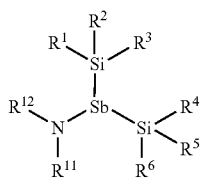
(C)

where $R^{2-10}$ are individually a hydrogen atom, an alkyl group or alkenyl group with 1 to 10 carbons as chain, branched, or cyclic, or an aromatic group; $R^1$ is individually a hydrogen atom, an alkyl group or alkenyl group with 2 to 10 carbons as chain, branched, or cyclic, or an aromatic group; $R^{11}$ and $R^{12}$ are individually an alkyl group or alkenyl group with 1 to 10 carbons as chain, branched, or cyclic, or an aromatic group; and if in structure (A), one of $R^{1-9}$ is phenyl, then the remaining of $R^{1-9}$ on that silicon bearing the phenyl are not both methyl; and if in structure (A) any of $R^{1-9}$ are $C^{1-3}$ or phenyl then not all of $R^{1-9}$ can be the same.

DETAILED DESCRIPTION OF THE INVENTION

The present invention relates to a class of antimony precursors, which generate antimony layers in ALD process. The antimony layer react with consequently deposited germanium and tellurium layers in ALD cycles to form GST ternary material films, which is suitable for PRAM devices.

GST materials in PRAM devices are normally deposited in the temperature range of 180°-300° C. It was found that the film deposited at 200° C. has the best chemical and structural properties. The ALD process requires precursors with high chemical reactivity and reaction selectivity. Currently existing precursors, such as dialkyltellium, trialkylantimony, and alkylgermanes do not have the required reactivity at given deposition conditions to be used in ALD cycles. Frequently, plasma is used to promote the deposition.

This invention provides silylantimony compounds as ALD precursors, which react with alcohols or water to generate an antimony layer. With consequent deposition of germanium and tellurium from tetraaminogermanium and organotellurium precursors, a GST film can be deposited on substrate with high conformality.

The present invention relates to a class of antimony precursors, which generate antimony layers in an ALD process. The antimony layer reacts with consequently deposited germanium and telluriumy layers in a plurality of ALD cycles to form GST ternary material films, which are suitable for PRAM devices. This invention discloses several silyl antimony precursors with high reactivity and thermal stability, and the chemistries to be used in an ALD process to deposit a GST film in conjunction with other chemicals.

This invention provides silylantimony compounds as ALD precursors, which react with alcohols or water to generate antimony atomic layer. With consequent deposition of germanium and tellurium from tetraaminogermanium and tellurium precursor, GST film can be deposited on substrate with high conformality.

The antimony precursors can contain trisilylantimony, disilylalkylantimony, disilylantimony, or disilylaminoantimony selected from the group consisting of:

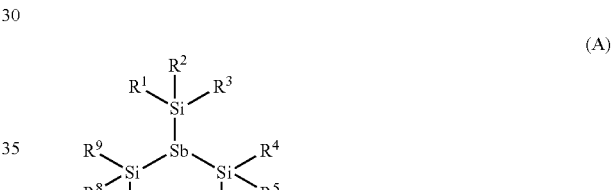
(A)

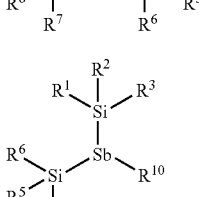
(B)

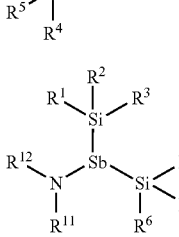
(C)

where $R^{2-10}$ are individually a hydrogen atom, an alkyl group or alkenyl group with 1 to 10 carbons as chain, branched, or cyclic, or an aromatic group. $R^1$ is individually a hydrogen atom, an alkyl group or alkenyl group with 2 to 10 carbons as chain, branched, or cyclic, or an aromatic group. $R^{11}$ and $R^{12}$ are individually an alkyl group or alkenyl group with 1 to 10 carbons as chain, branched, or cyclic, or an aromatic group. Preferably if in structure (A), one of $R^{1-9}$ is aromatic, then the remaining of $R^{1-9}$ on that silicon bearing the aromatic are not both methyl.

Silylantimony compounds are highly reactive with alcohols or water. The reaction generates elemental antimony at low temperature:

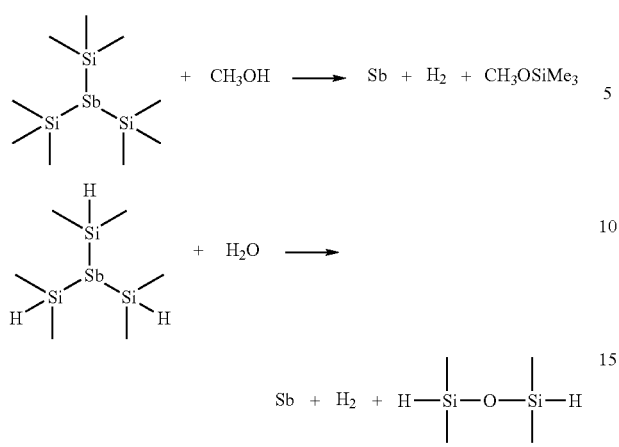

These reactions can take place at temperature range of room temperature to 300° C.

In an ALD process, the antimony precursors, alcohols, germanium and tellurium precursors, such as $(Me_2N)_4Ge$ and $(Me_3Si)_2Te$ (wherein "Me" is methyl) are introduced to a deposition chamber in a cyclic manner by vapor draw or direct liquid injection (DLI). The deposition temperature is preferably between 100° to 400° C.

The ALD reaction can be illustrated by the following scheme:

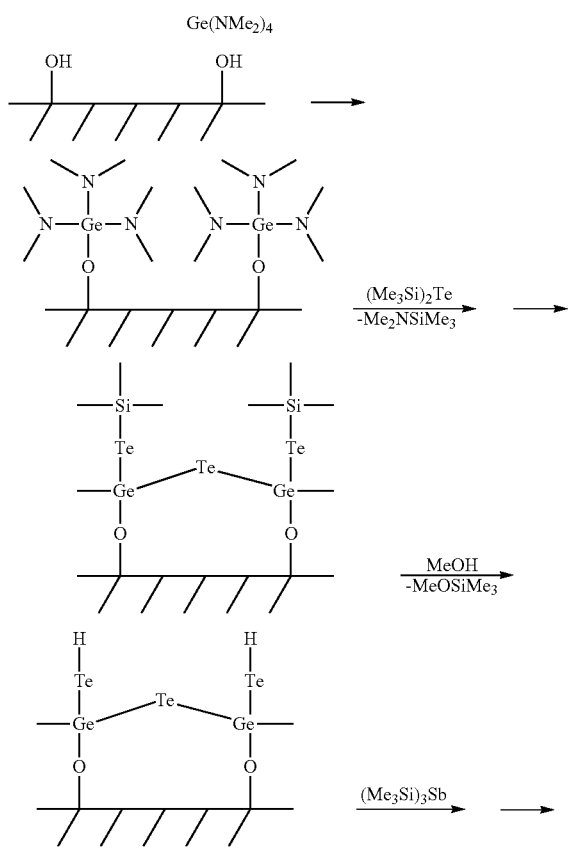

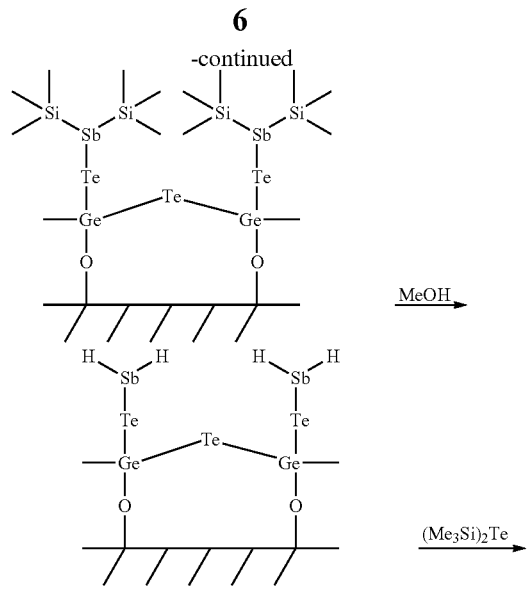

Step 1. Tetrakis(dimethylamino)germane is introduced and forms a molecular layer of aminogermane on the surface of the substrate.

Step 2. Hexamethyldisilyltellurium reacts with aminogermane layer to form Te—Ge bonds with elimination of dimethylaminotrimethylsilane. A Te layer with silyl substituents is formed.

Step 3. Methanol reacts with remaining silyl groups on the tellurium layer to form Te—H bonds and a volatile byproduct, methoxytrimethylsilane, which is removed by purge.

Step 4. Tris(trimethylsilyl)antimony is introduced and forms an antimony layer on the top of the tellurium layer.

Step 5. Methanol reacts with the remaining silyl groups on the antimony layer to form Sb—H bonds and a volatile byproduct, methoxytrimethylsilane, which is removed by purge.

Step 6. Hexamethyldisilyltellurium is introduced again and forms a tellurium layer.

Step 7. Methanol is introduced again to remove silyl groups on the tellurium.

An ALD cycle is then completely repeated, potentially many times, until the desired film thickness is achieved. The next cycle starts with Step 1, again, etc.

The silylantimony compounds used in this process are selected from the group consisting of:

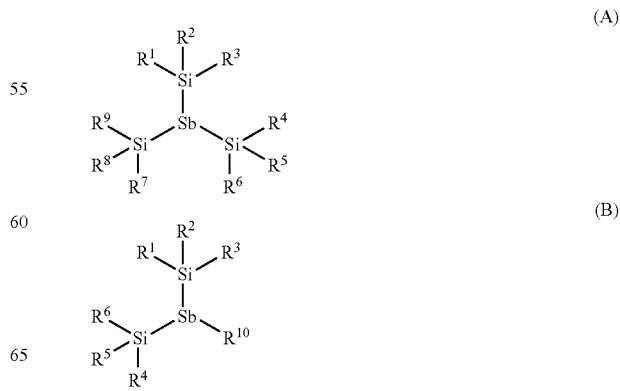

-continued

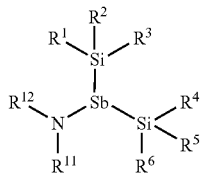
(C)

where $R^{2-10}$ are individually a hydrogen atom, an alkyl group or alkenyl group with 1 to 10 carbons as chain, branched, or cyclic, or an aromatic group. $R^1$ is individually a hydrogen atom, an alkyl group or alkenyl group with 2 to 10 carbons as chain, branched, or cyclic, or an aromatic group. $R^{11}$ and $R^{12}$ are individually an alkyl group or alkenyl group with 1 to 10 carbons as chain, branched, or cyclic, or an aromatic group. Preferably if in structure (A), one of $R^{1-9}$ is aromatic, then the remaining of $R^{1-9}$ on that silicon bearing the aromatic are not both methyl. Further, preferably, if in structure (A) any of $R^{1-9}$ are $C^{1-3}$ or phenyl then not all of $R^{1-9}$ can be the same.

Aminogermanes used in this process have the general formula:

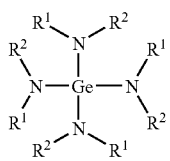

where $R^1$ and $R^2$ are individually alkyl groups with 1 to 10 carbons in linear, branched, or cyclic form.

The tellurium precursors can contain disilyltellurium, silylalkyltellurium, or silylaminotellurium selected from the group consisting of:

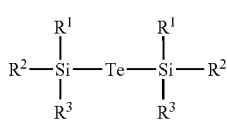
(a)

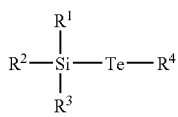
(b)

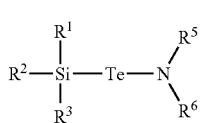
(c)

where $R^1$, $R^2$, $R^3$, $R^4$, $R^5$, and $R^6$ are independently hydrogen, alkyl groups having 1 to 10 carbons in linear, branched, or cyclic forms without or with double bonds, or aromatic groups.

Alcohols used in this process have the general formula:

ROH where R is an alkyl group with 1 to 10 carbons in linear, branched, or cyclic form.

EXAMPLE 1

Synthesis of Tris(trimethylsilyl)antimony 1.22 g (0.01 mol) of 200 mesh antimony powder, 0.72 g (0.03 mol) of lithium hydride, and 40 ml of tetrahydrofuran (THF) were placed in a 100 ml flask. With stirring, the mixture was refluxed for 4 hours. All of the black powder constituting antimony disappeared, and a muddy colored precipitate was formed. Then, the mixture was cooled down to −20° C.; 3.3 g (0.03 mol) of trimethylchlorosilane was added. The mixture was allowed to warm up to room temperature. After stirring for 4 hours, the mixture was filtered under inert atmosphere. The solvent was removed by distillation. Tris(trimethylsilyl)antimony was purified by vacuum distillation.

EXAMPLE 2

Synthesis of Tris(dimethylsilyl)antimony 1.22 g (0.01 mol) of 200 mesh antimony powder, 0.72 g (0.03 mol) of lithium hydride, and 40 ml of tetrahydrofuran (THF) were placed in a 100 ml flask. With stirring, the mixture was refluxed for 4 hours. All of the black powder constituting antimony disappeared, and a muddy colored precipitate was formed. Then, the mixture was cooled down to −20° C.; 2.83 g (0.03 mol) of diimethylchlorosilane was added. The mixture was allowed to warm up to room temperature. After stirring for 4 hours, the mixture was filtered under inert atmosphere. The solvent was removed by distillation. Tris(dimethylsilyl)antimony was purified by vacuum distillation.

EXAMPLE 3

Synthesis of Tris(dimethylsilyl)antimony 3.65 g (0.03 mol) of 200 mesh antimony powder, 2.07 g (0.09 mol) of sodium, 1.15 g (0.009 mol) of naphthalene, and 50 ml of THF were placed in a 100 ml flask. The mixture was stirred at room temperature for 24 hours. All of the black powder constituting antimony and sodium disappeared, and a muddy colored precipitate was formed. Then, the mixture was cooled down to −20° C.; 8.51 g (0.09 mol) of dimethylchlorosilane was added. The mixture was allowed to warm up to room temperature. After stirring for 4 hours, the mixture was filtered under inert atmosphere. The solvent was removed by distillation. Tris(dimethylsilyl)antimony was purified by vacuum distillation.

EXAMPLE 4

Generation of Antimony Film 0.05 g of Tris(dimethylsilyl)antimony was placed on the bottom of a 100 ml pyrex glass flask filled with nitrogen and fitted with a rubber septum. 0.1 g of methanol was added slowly with a syringe. A shiny black film started to deposit inside the glass wall of the flask. After a few minutes, the entire flask interior was coated with a dark gray/black antimony film.

The invention claimed is:
1. An ALD process for making a germanium-antimony-tellurium alloy film comprising the steps of:
  a) introducing into a deposition chamber an aminogermane with the general formula:

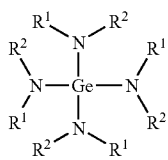

where $R^1$ and $R^2$ are individually in chain, branch or cyclic alkyl groups with 1 to 10 carbons, to form a molecular layer of aminogermane on the surface of the substrate;

b) introducing into the deposition chamber a tellurium precursor selected from the group consisting of:

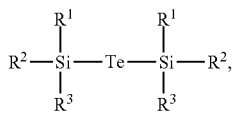

(a)

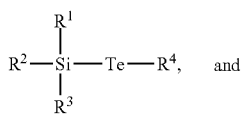

(b)

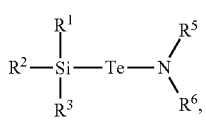

(c)

where $R^1$, $R^2$, $R^3$, $R^4$, $R^5$, and $R^6$ are independently hydrogen, alkyl groups having 1 to 10 carbons in linear, branched, or cyclic forms with or without double bonds, or aromatic groups, to react with the aminogermane layer to form a Te layer comprising Te-Ge bonds, wherein the Te comprises silyl substituents;

reacting the silyl substituents on the Te with an alcohol having the general formula of ROH, where R is an alkyl group with 1 to 10 carbon atoms in a linear, branched, or cyclic form, or an aromatic group, to form Te-H bonds;

d) introducing into the deposition chamber a silylantimony precursor selected from the group consisting of:

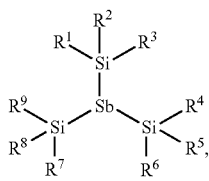

(A)

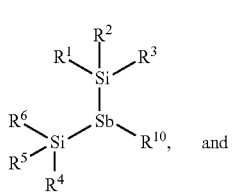

(B)

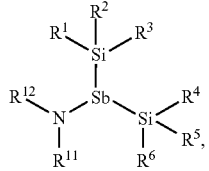

(C)

where $R^{2-10}$ are individually a hydrogen atom, an alkyl group or alkenyl group with 1 to 10 carbons as chain, branched, or cyclic, or an aromatic group; $R^1$ is individually a hydrogen atom, an alkyl group or alkenyl group with 2 to 10 carbons as chain, branched, or cyclic, or an aromatic group; $R^{11}$ and $R^{12}$ are individually an alkyl group or alkenyl group with 1 to 10 carbons as chain, branched, or cyclic, or an aromatic group, to form an Sb layer on top of the Te layer, wherein the Sb comprises silyl substituents; and reacting the silyl substituents on the Sb with (i) water and/or (ii) an alcohol having the general formula of ROH, where R is an alkyl group with 1 to 10 carbon atoms in a linear, branched, or cyclic form, or an aromatic group, to form Sb-H bonds..

2. The process of claim 1 wherein the silylantimony precursor is tris(trimethylsilyl)antimony.

3. The process of claim 1 wherein the steps are repeated.

4. The process of claim 1 wherein the temperature of the deposition chamber is between from 100° C. to 400° C.

5. The process of claim 1 wherein the alcohol is methanol.

6. An ALD process for depositing a metalic antimony layer on a substrate, the process comprising the step of:

reacting a silylantimony precursor with water or an alcohol to form an antimony layer, wherein the silylantimony precursor is selected from the group consisting of:

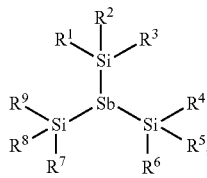

(A)

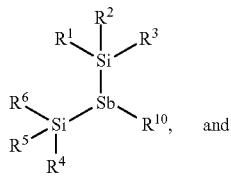

(B)

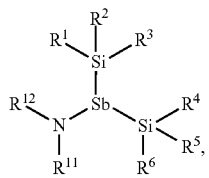

(C)

where $R^{2-10}$ are individually a hydrogen atom, an alkyl group or alkenyl group with 1 to 10 carbons as chain, branched, or cyclic, or an aromatic group; $R^1$ is individually a hydrogen atom, an alkyl group or alkenyl group with 2 to 10 carbons as chain, branched, or cyclic, or an aromatic group; $R^{11}$ and $R^{12}$ are individually an alkyl group or alkenyl group with 1 to 10 carbons as chain, branched, or cyclic, or an aromatic group.

7. The process of claim 6 wherein the alcohol is an alcohol having the general formula of ROH, where R is an alkyl group with 1 to 10 carbon atoms in a linear, branched, or cyclic form, or an aromatic group.

8. The process of claim 7 wherein the alcohol is methanol.

9. The process of claim 6 wherein the temperature of the reaction is between from room temperature to 300° C.

10. An ALD process comprising the steps of:

introducing into a deposition chamber a tellurium precursor selected from the group consisting of:

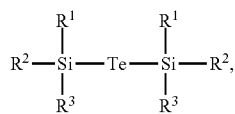 (a)

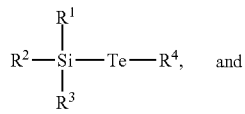 (b)

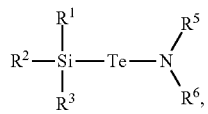 (c)

where $R^1$, $R^2$, $R^3$, $R^4$, $R^5$, and $R^6$ are independently hydrogen, alkyl groups having 1 to 10 carbons in linear, branched, or cyclic forms with or without double bonds, or aromatic groups, to form a Te layer comprising silyl substituents on the Te;

reacting the silyl substituents on the Te with an alcohol having the general formula of ROH, where R is an alkyl group with 1 to 10 carbon atoms in a linear, branched, or cyclic form, or an aromatic group, to form Te-H bonds;

introducing into the deposition chamber a silylantimony precursor selected from the group consisting of:

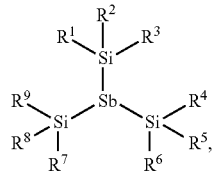 (A)

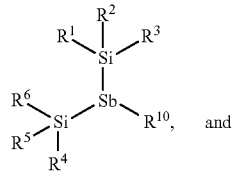 (B)

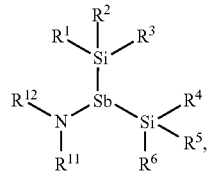 (C)

where $R^{2-10}$ are individually a hydrogen atom, an alkyl group or alkenyl group with 1 to 10 carbons as chain, branched, or cyclic, or an aromatic group; $R^1$ is individually a hydrogen atom, an alkyl group or alkenyl group with 2 to 10 carbons as chain, branched, or cyclic, or an aromatic group; $R^{11}$ and $R^{12}$ are individually an alkyl group or alkenyl group with 1 to 10 carbons as chain, branched, or cyclic, or an aromatic group, to form an Sb layer on top of the Te layer, wherein the Sb comprises silyl substituents; and reacting the substituents on the Sb with (i) water and/or (ii) an alcohol having the general formula of ROH, where R is an alkyl group with 1 to 10 carbon atoms in a linear, branched, or cyclic form, or an aromatic group, to form Sb-H bonds.

11. The process of claim 10 wherein the alcohol is methanol.

12. The process of claim 10 the temperature of the reaction is between from room temperature to 300° C.

* * * * *